US006867302B2

(12) United States Patent
Smith, III et al.

(10) Patent No.: US 6,867,302 B2
(45) Date of Patent: Mar. 15, 2005

(54) PROCESS FOR THE CATALYTIC SYNTHESIS OF BIARYLS AND POLYMERS FROM ARYL COMPOUNDS

(75) Inventors: Milton R. Smith, III, East Lansing, MI (US); Robert E. Maleczka, Dewitt, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 10/194,859

(22) Filed: Jul. 12, 2002

(65) Prior Publication Data

US 2003/0109713 A1 Jun. 12, 2003

Related U.S. Application Data

(60) Provisional application No. 60/332,092, filed on Nov. 21, 2001, and provisional application No. 60/305,107, filed on Jul. 13, 2001.

(51) Int. Cl.$^7$ ..................... C07D 213/14; C07D 213/08
(52) U.S. Cl. ................. 546/250; 556/7; 556/9; 556/12; 556/11; 556/13; 556/126; 556/182; 556/402; 540/302; 526/126; 502/7; 585/422; 562/7
(58) Field of Search .............................. 546/250; 556/7, 556/402, 9, 12, 11, 13, 126, 182; 526/126; 540/302; 502/7; 585/422; 562/7

(56) References Cited

FOREIGN PATENT DOCUMENTS

WO    WO 01/64688 A1 *  9/2003

OTHER PUBLICATIONS

Miyaura et al., Synth. Commun. 11: 1981, pp. 513–519.*

* cited by examiner

Primary Examiner—Elvis O. Price
(74) Attorney, Agent, or Firm—Ian C. McLeod

(57) ABSTRACT

A process for producing organic substituted aromatic or heteroaromatic compounds including biaryl and biheteroaryl compounds in a two-step reaction. In the first step, the aromatic or heteroaromatic compound is borylated in a reaction comprising a borane or diborane reagent (any boron reagent where the boron reagent contains a B—H, B—B or B—Si bond) and an iridium or rhodium catalytic complex. In the second step, a metal catalyst catalyzes the formation of the organic substituted aromatic or heteroaromatic compound from the borylated compound and an electrophile such as an aryl or organic halide, triflate ($OSO_2CF_3$), or nonaflate ($OSO_2C_4F_9$). The steps in the process can be performed in a single reaction vessel or in separate reaction vessels. The present invention also provides a process for synthesis of complex polyphenylenes starting from halogenated aromatic compounds.

24 Claims, 4 Drawing Sheets 16　　　　　　　　　17　　　　　　　　　18

19　　　　　　　　　21　　　　　　　　　20

22　　　　　　　　　23　　　　　　　　　24

25　　　　　　　　　26　　　　　　　　　27

PROCESS FOR THE CATALYTIC SYNTHESIS OF BIARYLS AND POLYMERS FROM ARYL COMPOUNDS

CROSS-REFERENCE TO RELATED APPLICATION

This application claims priority to Provisional Application No. 60/305,107, filed Jul. 13, 2001, and to Provisional Application No. 60/332,092, filed Nov. 21, 2001.

STATEMENT REGARDING FEDERALLY SPONSORED RESEARCH OR DEVELOPMENT

This invention was supported in part by National Institutes of Health, National Institute of General Medical Sciences Grant No. R01 GM63188-01 and in part by National Science Foundation Grant No. CHE-9817230. The U.S. government has certain rights in this invention.

REFERENCE TO A "COMPUTER LISTING APPENDIX SUBMITTED ON A COMPACT DISC"

Not Applicable.

BACKGROUND OF THE INVENTION

(1) Field of the Invention

The present invention relates to a process for producing organic substituted aromatic or heteroaromatic compounds including biaryl and biheteroaryl compounds in a two-step reaction. In the first step, the aromatic or heteroaromatic compound is borylated in a reaction comprising a borane or diborane reagent (any boron reagent where the boron reagent contains a B—H, B—B or B—Si bond) and an iridium or rhodium catalytic complex. In the second step, a metal catalyst catalyzes the formation of the organic substituted aromatic or heteroaromatic compound from the borylated compound and an electrophile such as an organic or aryl halide, triflate ($OSO_2CF_3$), or nonaflate ($OSO_2C_4F_9$). The steps in the process can be performed in a single reaction vessel or in separate reaction vessels. The present invention also provides a process for synthesis of complex polyphenylenes starting from halogenated aromatic compounds.

(2) Description of Related Art

Carbon-carbon bonds are the molecular "bricks and mortar" from which diverse architectures in living organisms and man-made materials are constructed. As the field of organic chemistry has evolved, numerous methods for carbon-carbon bond construction have been developed, ranging from classic examples, like the Diels-Alder reaction, to more recent metal-catalyzed processes such as olefin polymerizations and metatheses.

Substituted aromatic, and their heteroaromatic analogs, are abundant in natural and in synthetic materials. Consequently, controlled methods for linking aromatic rings via C—C sigma bonds have long been pursued by organic chemists. Activity in this regard intensified in the late 1970's during which Pd catalyzed methods for C—C bond construction emerged (Diederich and Stang, Metal-Catalyzed Cross-Coupling Reactions. Wiley-VCH, New York (1998)). Notably, the Pd catalyzed coupling of an arylboronic acid and an aryl halide disclosed by Miyaura and Suzuki,

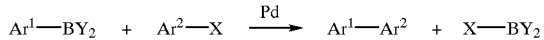

(Y=OH; X=halide) has become a method of choice for preparing biaryls since it is performed under mild conditions, tolerant of diverse functionality, and highly selective (Miyaura et al., Synth. Commun. 11: 513–519 (1981)). Subsequent developments in metal-catalyzed cross-couplings of organoboron compounds and organic halides have yielded practical C—C bond forming strategies that complement existing methodology (Suzuki, Organomet. Chem. 576; 147–168 (1999)). Today the Miyaura-Suzuki reaction is routinely applied in high-throughput screening for drug discovery (Sammelson and Kurth, Chem. Rev. 101: 137–202 (2001)), in the final steps of convergent natural product syntheses (Chemler and Danishefsky, Org. Lett. 2: 2695–2698 (2000)), and in the synthesis of conjugated organic materials (Schlütter, J. Polym. Sci. A-Polym. Chem. 39: 1533–1556 (2001)).

Arylboron reagents are typically synthesized in a multi-step process such as that shown below.

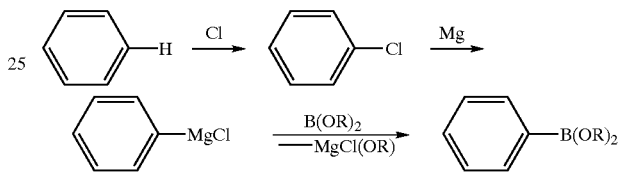

Shorter routes that avoid undesirable halogenated aromatic intermediates would be attractive. Towards this end, theoretical estimates of B—H and B—C bond enthalpies gave credence to organoborane synthesis via the thermal dehydrogenative coupling of B—H and C—H bonds as shown below (Rablen et al., J. Am. Chem. Soc. 116: 4121–4122 (1994)).

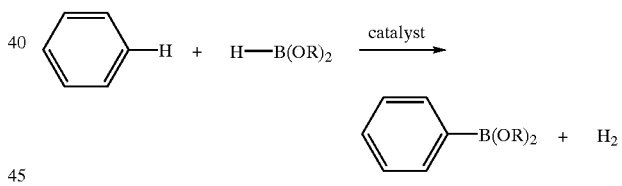

Some key steps in putative catalytic cycles for this process had been established with Hartwig's (Waltz et al., J. Am. Chem. Soc. 117: 11357–11358 (1995); Waltz and Hartwig, Science 277: 211–213 (1997)) and Marder's reports of stoichiometric borylations of arenes, alkenes, and alkanes by metal boryl complexes (M-$BR_2$). Although arene activation products were not mentioned, small peaks in the GC-MS trace with masses consistent with toluene borylation products were assigned in the Supplementary Material to Nguyen et al., Am. Chem. Soc. 115,9329–9330 (1993).

While Hartwig has developed elegant photochemical methods for hydrocarbon borylation using catalytic amounts of metal complexes (Chen and Hartwig, Angew. Chem. Int. Ed. 38: 3391–3393 (1999)), thermal, catalytic borylations of unactivated hydrocarbons had not been documented prior to our report in 1999 (Iverson and Smith, III, J. Am. Chem. Soc. 121: 7696–7697 (1999)). Since then, borylation of aliphatic and alkyl branched alicyclic hydrocarbons at a primary C—H hydrocarbon bond under thermal conditions using a rhodium catalytic complex which includes an electron donor ligand was disclosed in WO 01/64689 A1 and U.S. patent application Ser. No. 0039349 A1, both to Chen et al., and borylation of cyclic hydrocarbons at a secondary or aromatic C—H cyclic hydrocarbon bond using the above rhodium catalytic complex was disclosed in WO 01/64688 A1 to Chen et al.

Currently, because C—C coupling of a hydrocarbon requires a multi-step process to produce a borylated hydrocarbon, which is then reacted with a hydrocarbon halide to couple the hydrocarbons, it would be desirable to have a process wherein the borylation and the C—C coupling are performed in fewer steps or in the same reaction vessel, or both. Therefore, a need remains for a process for C—C coupling of hydrocarbons which can be performed in fewer steps and preferably, in the same reaction vessel.

SUMMARY OF THE INVENTION

The present invention provides a process for producing organic substituted aromatic compounds (which includes organic substituted heteroaromatic compounds and biaryl compounds) in a two-step reaction. In the first step, the aromatic compound is borylated in a reaction comprising a borane or diborane reagent (any boron reagent where the boron reagent contains a B—H, B—B or B—Si bond) and an iridium or rhodium catalytic complex. In the second step, a metal catalyst catalyzes the formation of the organic substituted aromatic compound from the borylated compound and an electrophile such as an aryl or organic halide, triflate ($OSO_2CF_3$), or nonaflate ($OSO_2C_4F_9$). The steps in the process can be performed in a single reaction vessel or in separate reaction vessels. The present invention also provides a process for synthesis of complex polyphenylenes starting from halogenated aromatic compounds.

Therefore, the present invention provides a process for producing a substituted aromatic compound, which comprises (a) reacting an aromatic compound selected from the group consisting of an aryl, a six membered heteroaromatic compound, and a five membered heteroaromatic compound with a borane selected from the group consisting of a borane with a B—H, B—B, and B—Si bond in the presence of a catalytically effective amount of an iridium or rhodium complex with three or more substituents, and an organic ligand selected from the group consisting of phosphorus, carbon, nitrogen, oxygen, and sulfur organic ligands to form an aromatic boron compound; and (b) reacting the aromatic boron compound with an organic compound selected from the group consisting of halide, triflate, and nonaflate in the presence of a catalytically effective amount of a metal catalyst wherein the aromatic group of the organic compound is coupled to the aromatic group of the aromatic boron compound to produce the substituted aromatic compound.

The present invention further provides process for producing an organic substituted aryl or heteroaryl compound, which comprises (a) reacting in a reaction vessel a first aromatic compound selected from the group consisting of an aryl, a six membered heteroaromatic compound, and a five membered heteroaromatic compound with a borane selected from the group consisting of a borane with a B—H, B—B, and B—Si bond in the presence of a catalytically effective amount of an iridium or rhodium complex with three or more substituents, and an organic ligand selected from the group consisting of phosphorus, carbon, nitrogen, oxygen, and sulfur organic ligands to form an aromatic boron compound; and (b) reacting the aromatic boron compound formed in the reaction vessel with an organic compound selected from the group consisting of halide, triflate, and nonaflate in the presence of a catalytically effective amount of a metal catalyst wherein the aromatic group of the organic compound is coupled to the aromatic group of the aromatic boron compound to produce the organic substituted aryl or heteroaryl compound.

The present invention further provides a process for producing a polyphenylene, which comprises (a) reacting a mixture of aromatic compounds with one to five halogen groups and a borane in the presence of a catalytically effective amount of an iridium or rhodium complex with three or more substituents, and a phosphorus, carbon, nitrogen, oxygen, or sulfur organic ligand to form a mixture of borylated aromatic compounds; and (b) reacting the mixture of borylated aromatic compounds in the presence of a catalytically effective amount of a metal catalyst wherein the borylated aromatic compounds in the mixture are cross-coupled to produce the polyphenylene.

The present invention further provides process for producing a polyphenylene, which comprises (a) reacting a mixture of aromatic compounds and a borane in the presence of a catalytically effective amount of an iridium or rhodium complex with three or more substituents, and a phosphorus, carbon, nitrogen, oxygen, or sulfur organic ligand to form a mixture of borylated aromatic compounds; and (b) reacting the mixture of borylated aromatic compounds with a mixture of halogenated aromatic compounds with at least two halogen groups in the presence of a catalytically effective amount of a metal catalyst wherein the borylated aromatic compounds in the mixture are cross-coupled to the halogenated aromatic compounds to produce the polyphenylene.

In a further embodiment of the above processes, the three or more substituents excludes hydrogen.

In a further embodiment of the above processes, the iridium complex is selected from the group consisting of (Cp*)Ir(H)$_2$(Me$_3$P), (Cp*)Ir(H)(BPin)(Me$_3$P), (Cp*)Ir(H)(C$_6$H$_5$)(Me$_3$P), (Ind)Ir(COD), (Ind)Ir(dppe), (MesH)Ir(BPin)(B(OR)$_2$)$_2$, ((R$_1$)$_3$P)$_3$Ir(B(OR$_2$)$_2$)$_3$, (R$_1$)$_2$P)$_2$Ir(BPin)$_3$, (((R$_1$)$_2$P)$_3$Ir((R$_2$O)$_2$B)$_3$)$_2$, ((R$_1$)$_3$P)$_4$Ir(BPin), ((R$_1$)$_3$P)$_2$Ir(BPin)$_3$, (MesH)Ir(BPin)$_3$, and (IrCl(COD))$_2$, (PMe$_3$)$_2$IrH$_5$, ((R$_1$)$_3$P)$_2$IrH$_5$, and ((R)$_3$P)$_2$IrH$_x$(B(OR$_2$)$_2$)$_{5-x}$ where x is 0–4, wherein Cp* is 1,2,3,4,5-methylcyclopentadienyl, BPin is pinacolborane, Me is methyl, H is hydrogen, P is phosphorus, Ind is indenyl, COD is 1,5-cyclooctadiene, MesH is mesitylene, and wherein R, R$_1$, and R$_2$ are hydrogen, linear or branched alkyl containing 1 to 8 carbons, aryl, or a carbon in a cyclic structure.

In a further embodiment of the above processes, the iridium complex is (Ind)Ir(COD) wherein Ind is indenyl and COD is 1,5-cyclooctadiene, (MesH)Ir(BPin)$_3$ wherein MesH is mesitylene and BPin is pinacolborane, or (IrCl(COD))$_2$ wherein COD is 1,5-cyclooctadiene.

In a further embodiment of the above processes, the rhodium complex is selected from the group consisting of (Cp*)Rh(H)$_2$ (Me$_3$P), (Cp*)Rh(H)(BPin)(Me$_3$P), (Cp*)Rh(H)(C$_6$H$_5$)(Me$_3$P), and (Cp*)Rh(hexamethylbenzene), wherein Cp* is 1,2,3,4,5-methylcyclopentadienyl, BPin is pinacolborane, Me is methyl, H is hydrogen, and P is phosphorus.

In a further embodiment of the above processes, the phosphorus organic ligand is selected from the group consisting of trimethyl phosphine (PMe$_3$), 1,2-bis(dimethylphosphino)ethane (dmpe), and 1,2-bis(diphenylphosphino)ethane (dppe).

In a further embodiment of the above processes, the borane is a borane ester.

In a further embodiment of the above processes, the borane is pinacolborane. In a further embodiment of the above processes, the metal is palladium.

In a further embodiment of the above processes, the metal catalyst complex is selected from Pd(PPh$_3$)$_4$, Pd$_2$(dba)$_3$/P($^t$Bu)$_3$, PdCl$_2$(dppf), Pd(OAc)$_2$/PCy$_3$ wherein P is phosphorus and Ph is phenyl, dba is dibenzylideneacetone, $^t$Bu is tert-butyl, dppf is diphenylphosphinoferrocene.

OBJECTS

It is an object of the present invention to provide a process for producing organic substituted aryl compounds and polyphenylenes.

It is a further object of the present invention to provide a two-step process for producing organic substituted aryl compounds and polyphenylenes.

It is a further object of the present invention to provide a two-step process that can be carried out in a single reaction vessel.

These and other objects of the present invention will become increasingly apparent with reference to the following drawings and preferred embodiments.

DETAILED DESCRIPTION OF THE DRAWINGS

FIG. 1 shows the formulas for precatalysts 1 to 15. CP* is 1,2,3,4,5-methylcyclopentadienyl, BPin is pinacolborane, Me is methyl, H is hydrogen, P is phosphorus, Ind is indenyl, COD is 1,5-cyclooctadiene, MesH is mesitylene, and wherein R, R$_1$, and R$_2$ are each selected from the group consisting of hydrogen, linear or branched alkyl containing 1 to 8 carbons, aryl, and a carbon in a cyclic structure.

FIG. 2 shows the formulas for precatalysts 16 to 27. Y$_4$, Y$_5$, and Y$_6$ are each selected from the group consisting of hydrogen, halide, alkyl, aryl, alkoxide (—O(R$_{11}$)), and amide (—N(R$_{12}$)(R$_{13}$)) wherein R$_{11}$, R$_{12}$, and R$_{13}$ are each selected from the group consisting of hydrogen, linear alkyl containing 1 to 8 carbon atoms, branched alkyl containing 1 to 8 carbons, and a carbon in a cyclic structure; R$_{14}$, R$_{15}$, and R$_{16}$ are each selected from the group consisting of hydrogen, linear alkyl, branched alkyl, and a carbon in a cyclic structure; (PY$_7$P) is R$_{18}$R$_{19}$P—Y$_7$—PR$_{20}$R$_{21}$ wherein R$_{18}$, R$_{19}$, R$_{20}$, and R$_{21}$ are each selected from the group consisting of hydrogen, linear alkyl containing 1 to 8 carbon atoms, branched alkyl containing 1 to 8 carbons, and a carbon in a cyclic structure, and Y$_7$ is a chain containing 1 to 12 carbons; (P⌒P) is of the formula

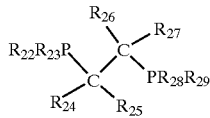

wherein R$_{22}$, R$_{23}$, R$_{24}$, R$_{25}$, R$_{26}$, R$_{27}$, R$_{28}$, and R$_{29}$ are each selected from the group consisting of alkyl chains, carbocyclic rings, and aryl groups; and BY is a boron moiety.

DETAILED DESCRIPTION OF THE INVENTION

Figure 1:
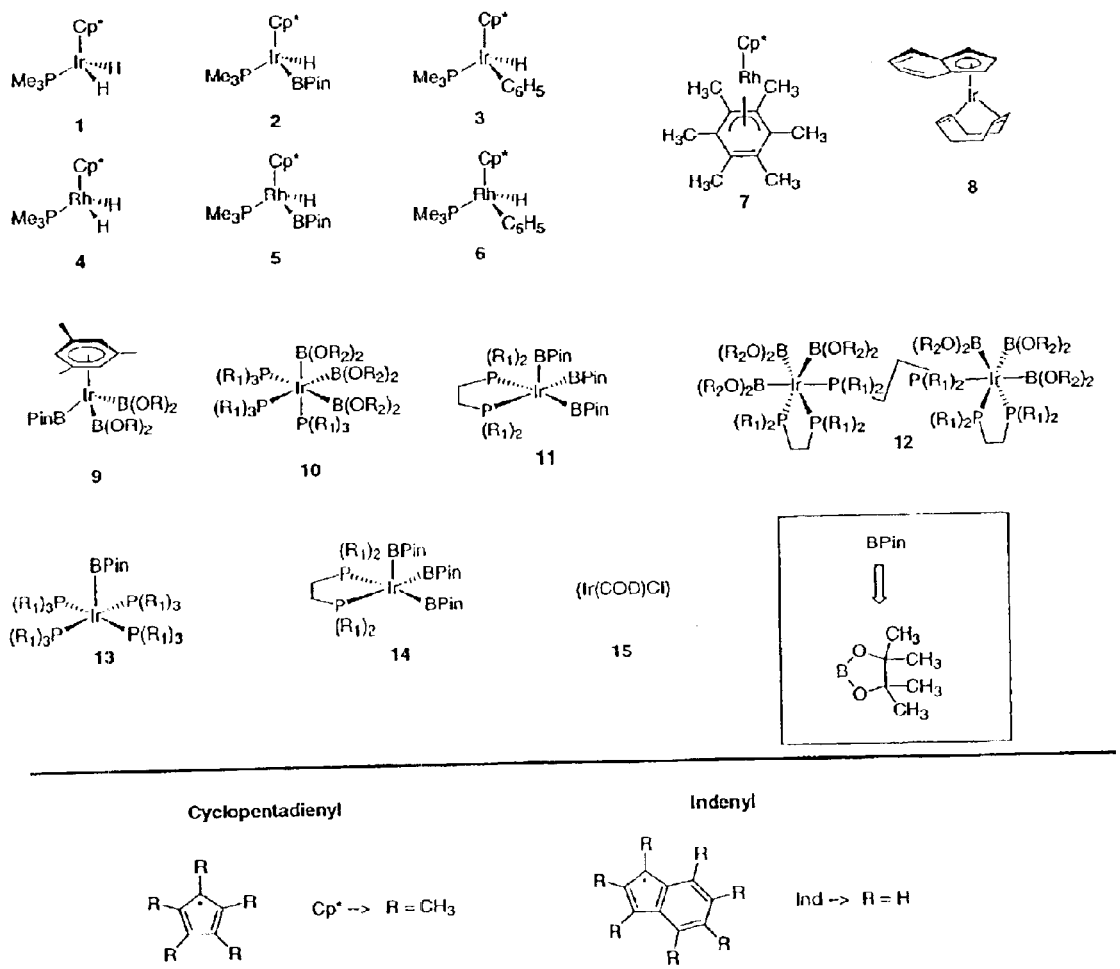

All patents, patent applications, provisional patent applications, government publications, government regulations, and literature references cited in this specification are hereby incorporated herein by reference in their entirety. In case of conflict, the present description, including definitions, will control.

For convenience, wherever the term "aromatic" is used alone, it is to be construed to include both aromatic and heteroaromatic compounds selected from the group consisting of aryl, six membered heteroaromatic compounds, and five membered heteroaromatic compounds and the wherever the term "organic substituted aromatic compounds" is used alone, it is to be construed to include both organic substituted aromatic and heteroaromatic compounds and biaryl compounds.

The present invention provides a process for producing organic substituted aromatic and heteroaromatic compounds including biaryl and biheteroaryl compounds, which comprises in a first step, reacting an aromatic or heteroaromatic compound with a borane or diborane containing a B—H, B—B or B—Si bond, but preferably a borane ester, in the presence of a catalytically effective amount of an iridium or rhodium complex with three or more substituents to produce a borylated aromatic or heteroaromatic intermediate; and in a second step, reacting the borylated aromatic or heteroaromatic intermediate with an organic electrophile such as an aryl halide, triflate (OSO$_2$CF$_3$), or nonaflate (OSO$_2$C$_4$F$_9$), or the like, in the presence of a catalytically effective amount of a metal catalyst wherein the aryl group of the aryl or organic halide, triflate, or nonaflate is coupled to the aromatic or heteroaromatic group of the borylated compound to produce the organic substituted aromatic or heteroaromatic compound, including biaryl.

The borylation of an aromatic or heteroaromatic substrate and the subsequent coupling of the borylated aromatic or heteroaromatic intermediate with a second sp$^2$-hybridized halocarbon can be performed in a single reaction vessel as shown in Scheme 1.

Scheme 8

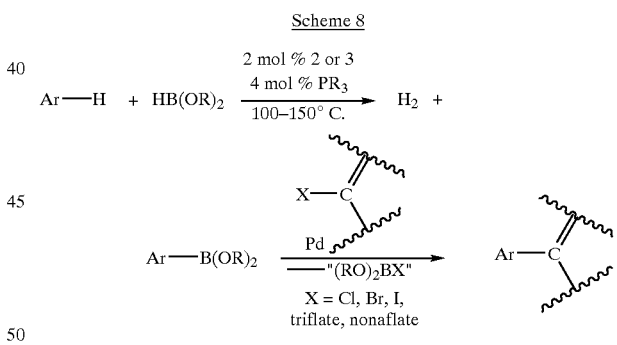

The present invention further provides a process for producing a polyphenylene, which in a first step comprises reacting a mixture of aromatic compounds with one to five halogen groups and a borane or diborane containing a B—H, B—B or B—Si bond, but preferably a borane ester, in the presence of a catalytically effective amount of an iridium or rhodium complex with three or more substituents, to form a mixture of borylated aromatic intermediates; and in a second step, reacting the mixture of borylated aromatic intermediates in the presence of a catalytically effective amount of a metal catalyst wherein the borylated aromatic intermediates in the mixture are cross-coupled to produce the polyphenylene. See FIG. 3B for an example of the process. The mixture of aromatic compounds can contain all of one type of aromatic compound or a mixture of different types of aromatic compounds.

The present invention further provides a process for producing a polyphenylene, which in a first step comprises reacting a mixture of aromatic compounds and a borane or diborane containing a B—H, B—B or B—Si bond, but preferably a borane ester, in the presence of a catalytically effective amount of an iridium or rhodium complex with three or more substituents, to form a mixture of borylated aromatic intermediates; and in a second step, reacting the mixture of borylated aromatic intermediates with a mixture of halogenated aromatics with at least two halogen groups in the presence of a catalytically effective amount of a metal catalyst wherein the borylated aromatic intermediates in the mixture are cross-coupled to the halogenated aromatic compounds to produce the polyphenylene. The mixture of aromatic compounds can contain all of one type of aromatic compound or a mixture of different types of aromatic compounds. The process is shown in Scheme 2 below.

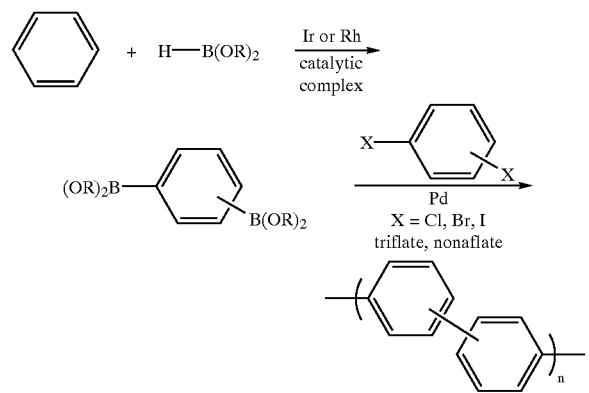

In Scheme 2, $HB(OR)_2$ is preferably BPin.

The preferred catalysts for producing the borylated intermediates in the first step of the process comprise iridium (Ir) or rhodium (Rh) in a complex with three or more substituents, preferably excluding hydrogen, bonded to the Ir or Rh and preferably, further including a phosphorus organic ligand, which is at least in part bonded to the Ir or Rh. The process for forming B—C bonds between boranes and sp$^2$-hybridized C—H bonds to produce organoboron intermediates such as ring-substituted arenes (or aryl boronate esters and acids) according is shown in Scheme 3.

Scheme 3

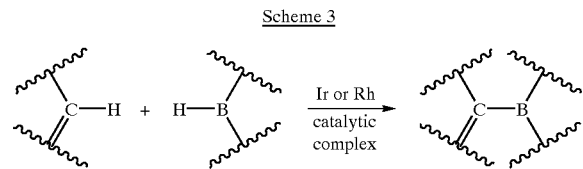

The direct route to aromatic or heteroaromatic boronate esters and acids in the first step produces intermediates which are versatile transfer reagents in the second step of the process of the present invention. The boron in these transfer reagents serves as a mask for a broad range of heteroatoms and functional groups during the catalytic cross-coupling reactions of C—B and C—X (X is Cl, Br, I, triflate, nonaflate) groups in the second step to yield new C—C bonds as shown in scheme 4.

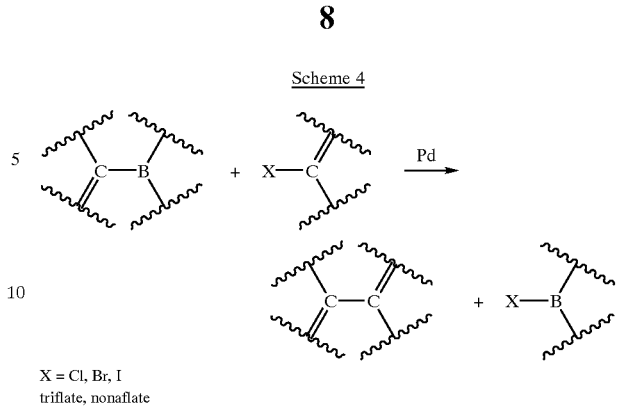

Scheme 4

X = Cl, Br, I
triflate, nonaflate

The above two-step process is particularly useful in the pharmaceutical industry for drug manufacturing and for synthesis of compounds in drug discovery. Thus, the present invention further provides catalyst kits that can be used for general couplings in drug discovery applications.

Preferably, the B—C bond-forming reaction between a borane and an sp$^2$-hybridized C—H bond to produce a ring substituted arene in the first step is catalyzed by a catalyst comprising Ir and Rh in a complex with three or more substituents, preferably excluding hydrogen as a substituent, bonded to the Ir or Rh and further preferably, an organic ligand selected from the group consisting of phosphorus, carbon, nitrogen, oxygen, and sulfur organic ligands. For example, phosphorus organic ligands, organic amines, imines, nitrogen heterocycles, ethers, and the like. Preferably, the ligand is in a molar ratio between about 1 to 3 and 1 to 1, wherein the organic ligand is at least in part bonded to the iridium or rhodium.

Effective precatalysts for forming the B—C bonds can be grouped into two families: those that contain cyclopentadienyl (Cp*, $C_5R_5$ wherein R is $CH_3$) or indenyl (Ind, $C_9R_7$ wherein R is H) ligands and those that contain phosphine ligands. Included are compounds that contain both the Cp* and the Ind ligands and the phosphine ligands.

Preferably, the Ir catalytic composition for the first step of the process comprises one of the following: $(ArH)Ir(BY)_3$ wherein ArH is selected from the group consisting of aromatic, heteroaromatic, polyaromatic, and heteropolyaromatic hydrocarbon and wherein BY is a boron moiety; $(MesH)Ir(BY)_3$ wherein MesH is mesitylene and wherein BY is a boron moiety; $(P(Y_4)(Y_5)(Y_6))_3Ir\ (H)_n(BY)_{3-n}$ wherein $Y_4$, $Y_5$, and $Y_6$ are each selected from the group consisting of hydrogen, halide, alkyl, aryl, alkoxide (—O $(R_{11})$), and amide (—N$(R_{12})$ $(R_{13})$) wherein $R_{11}$, $R_{12}$, and $R_{13}$ are each selected from the group consisting of hydrogen, linear alkyl containing 1 to 8 carbon atoms, branched alkyl containing 1 to 8 carbons, and a carbon in a cyclic structure, wherein n is 0, 1, or 2, and wherein BY is a boron moiety; $(P(R_{14})(R_{15})(R_{16}))_3Ir\ (H)_n(BY)_{3-n}$ wherein $R_{14}$, $R_{15}$, and $R_{16}$ are each selected from the group consisting of hydrogen, linear alkyl, branched alkyl, and a carbon in a cyclic structure, wherein n is 0, 1, or 2, and wherein BY is a boron moiety; $(P(Y_4)(Y_5)(Y_6))_3Ir\ (H)(R_{13})(BY)$ wherein $Y_4$, $Y_5$, and $Y_6$ are as above, wherein $R_{13}$ is selected from the group consisting of a linear alkyl containing 1 to 8 carbon atoms, branched alkyl containing 1 to 8 carbons, aryl, and a carbon in a cyclic structure, and wherein BY is a boron moiety; $(P(R_{14})(R_{15})(R_{16}))_3Ir\ (H)(R_{17})(BY)$ wherein $R_{14}$, $R_{15}$, and $R_{16}$ are as above; $R_{17}$ is as above, and wherein BY is a boron moiety; $\{(PY_7P)\ Ir(BY)_3\}_2\ (\mu_2\text{-}(PY_7P))$ (16) wherein BY is a boron moiety, wherein $(PY_7P)$ is $R_{18}R_{19}P$—$Y_7$—$PR_{20}R_{21}$ wherein $R_{18}$, $R_{19}$, $R_{20}$, and $R_{21}$ are each selected from the group consisting of hydrogen, linear alkyl containing 1 to 8 carbon atoms, branched alkyl containing 1 to 8 carbons, and a carbon in a cyclic structure, and wherein $Y_7$ is a chain containing 1 to 12 carbons; $(PY_7P)(P(Y_4)(Y_5)(Y_6))Ir(BY)_3$ (17) wherein BY is a boron moiety, wherein $Y_4$, $Y_5$, and $Y_6$ are as above, and wherein $(PY_7P)$ is as above; $(PY_7P)(P(R_{10})(R_{11})(R_{12}))Ir(BY)_3$ (18) wherein BY is a boron moiety, wherein $R_{14}$, $R_{15}$, and $R_{16}$ are as above, wherein $(PY_7P)$ is as above; $\{(P\frown P)Ir(BY)_3\}_2(\mu_2\text{-}(P\frown P))$ (19) wherein BY is a boron moiety and wherein $(P\frown P)$ is of the formula

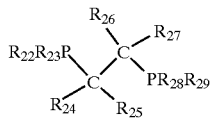

wherein $R_{22}$, $R_{23}$, $R_{24}$, $R_{25}$, $R_{26}$, $R_{27}$, $R_{28}$, and $R_{29}$ are each selected from the group consisting of alkyl chains, carbocyclic rings, and aryl groups; $(P\frown P)(P(Y_4)(Y_5)(Y_6))Ir(BY)_3$ (20) wherein BY is a boron moiety, wherein $Y_4$, $Y_5$, and $Y_6$ are as above, and wherein $(P\frown P)$ is as above; $(P\frown P)(P(R_{14})(R_{15})(R_{16}))Ir(BY)_3$ (21) wherein BY is a boron moiety, wherein $R_{14}$, $R_{15}$, and $R_{16}$ are as above, and wherein $(P\frown P)$ is as above; $(PY_7P)Ir(BY)_3$ (22) wherein BY is a boron moiety, and wherein and $(PY_7P)$ is as above; $(P\frown P)Ir(BY)_3$ (23) wherein BY is a boron moiety, and wherein $(P\frown P)$ is as above; $(P(Y_4)(Y_5)(Y_6))_4Ir(BY)$ wherein $Y_4$, $Y_5$, and $Y_6$ are as above and BY is a boron moiety; $(P(R_{14})(R_{15})(R_{16}))_4Ir(BY)$ wherein $R_{14}$, $R_{15}$, and $R_{16}$ are as above and BY is a boron moiety; $(PY_7P)(P(Y_4)(Y_5)(Y_6))_2Ir(BY)$ (24) wherein BY is a boron moiety, wherein $Y_4$, $Y_5$, and $Y_6$ are above, and wherein $(PY_7P)$ is as above; $(P\frown P)(P(Y_4)(Y_5)(Y_6))_2Ir(BY)$ (25) wherein BY is a boron moiety, wherein $Y_4$, $Y_5$, and $Y_6$ are as above, and wherein $(P\frown P)$ is as above; $(PY_7P)(P(R_{14})(R_{15})(R_{16}))_2Ir(BY)$ (26) wherein BY is a boron moiety, $R_{14}$, $R_{15}$, and $R_{17}$ are as above, and wherein $(PY_7P)$ is as above; $(P\frown P)(P(R_{14})(R_{15})(R_{16}))_2Ir(BY)$ (27) wherein BY is a boron moiety, wherein $R_{14}$, $R_{15}$, and $R_{16}$ are as above, and wherein $(P\frown P)$ is as above.

Examples of catalytic compositions comprising iridium include those selected from the group consisting of $(Cp^*)Ir(H)_2(Me_3P)$ (1), $(Cp^*)Ir(H)(BPin)(Me_3P)$ (2), $(CP^*)Ir(H)(C_6H_5)(Me_3P)$ (3), $(Ind)Ir(COD)$ (8), $(MesH)Ir(BPin)(B(OR)_2)$ (9), $((R_1)_3P)_3Ir(B(OR_2)_2)_3$ (10), $(R_1)_2P)_2Ir(BPin)_3$ (11), $(((R_1)_2P)_3Ir((R_2O)_2B)_3)_2$ (12), $((R_1)_3P)_4Ir(BPin)$ (13), $((R_1)_2P)_2Ir(BPin)_3$ (14), $(MesH)Ir(BPin)_3$ (9 wherein $B(OR)_2$ is BPin), $IrCl(COD)$ (15) and $(IrCl(COD))_2$, wherein CP* is 1,2,3,4,5-methylcyclopentadienyl, BPin is pinacolborane, Me is methyl, H is hydrogen, P is phosphorus, Ind is indenyl, COD is 1,5-cyclooctadiene, MesH is mesitylene, and wherein R, $R_1$, and $R_2$ are each selected from the group consisting of hydrogen, linear or branched alkyl containing 1 to 8 carbons, aryl, and a carbon in a cyclic structure.

Preferably, the Rh catalytic composition for the first step comprises one of the following: $(Cp')(P(Y_4)(Y_5)(Y_6))Rh(H)_n(BY)_{2-n}$ wherein $Y_4$, $Y_5$, and $Y_6$ are as above, wherein n is 0 or 1, wherein BY is a boron moiety, and wherein Cp' is of the formula

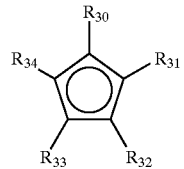

wherein $R_{30}$, $R_{31}$, $R_{32}$, $R_{33}$, and $R_{34}$ are each selected from the group consisting of hydrogen, alkyl chains, carbocyclic rings, and aryl groups; and $(Cp')(P(R_{14}(R_{15})(R_{16}))Rh(H)_n(BY)_{2-n}$, wherein $R_{14}$, $R_{15}$, and $R_{16}$ are as above; n is 0 or 1, wherein BY is a boron moiety; and wherein Cp' is as above.

Examples of catalytic compositions comprising rhodium include those selected from the group consisting of $(Cp^*)Rh(H)_2(Me_3P)$ (4), $(Cp^*)Rh(H)(BPin)(Me_3P)$ (5), $(CP^*)Rh(H)(C_6H_5)(Me_3P)$ (6), and $(Cp^*)Rh(hexamethylbenzene)$ (7), wherein CP* is 1,2,3,4,5-methylcyclopentadienyl, BPin is pinacolborane, Me is methyl, H is hydrogen, and P is phosphorus.

In the above catalytic compositions, preferably the BY boron moiety selected from the group consisting of

Figure 2:
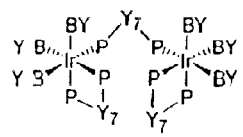
Figure 2:
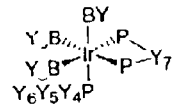
Figure 2:
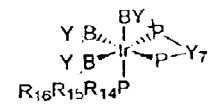
Figure 2:
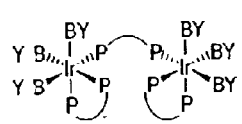
Figure 2:
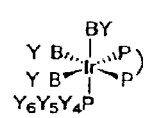
Figure 2:
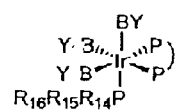
Figure 2:
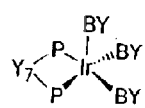
Figure 2:
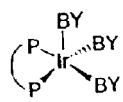
Figure 2:
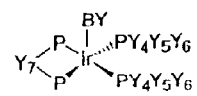
Figure 2:
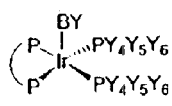
Figure 2:
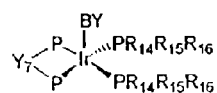
Figure 2:
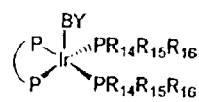

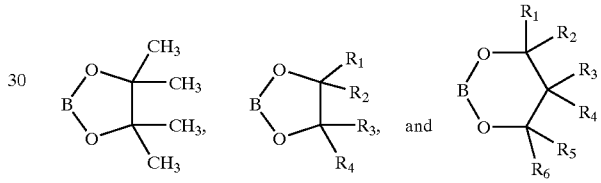

wherein $R_1$, $R_2$, $R_3$, $R_4$, $R_5$, and $R_6$ are each selected from the group consisting of hydrogen, linear alkyl containing 1 to 8 carbon atoms, branched alkyl containing 1 to 8 carbons, and a carbon in a cyclic structure. FIGS. 1 and 2 show the structures of precatalysts 1 to 15 and 16 to 27, respectively.

While the precatalysts can under particular reaction conditions catalyze the borylation of particular ring-substituted arenes, the reactions proceed more efficiently when an organic ligand such as phosphine ligands (phosphorus organic ligands) are included in the reaction mixture. The addition of phosphine ligands to the reaction generates active catalysts which can produce ring-substituted arene boranes (aryl boronate esters and acids) with low catalyst loading. The fact that phosphine-containing species can catalyze borylation is important because numerous phosphines are commercially available. Furthermore, the selectivities of the borylation can be altered as a function of the phosphine ligand that is added. Examples of phosphine ligands include, but are not limited to, trimethyl phosphine ($PMe_3$), 1,2-bis(dimethylphosphino)ethane (dmpe), 1,2-bis(diphenylphosphino)ethane (dppe), $Cy_3P$, and $Ph_3P$.

For example, precatalyst 8 can be obtained in two high-yielding steps from the common iridium starting material, $IrCl_3(H_2O)_x$. Precatalyst 9 can be prepared by reacting 8 with approximately 5 equivalents of pinacolborane (HBPin) in mesitylene solvent. It was discovered that commercially available precatalyst 15 will also catalyze borylations. While all of the precatalysts have similar activities for many substrates, borylations of particular arenes exhibit a remarkable precatalyst dependence.

In the absence of phosphine ligands, compound 8 catalyzes the borylation of benzene by HBPin, but relatively high catalyst loading and long reaction times are required to prepare PhBPin in reasonable yields. At temperatures above 80° C., decomposition to Ir metal occurs, which halts catalysis. Compound 9 is not effective in catalysis without the addition of phosphine.

Addition of phosphine ligands to solutions of compound 8 and 9 generates active catalysts for the production of aryl boronic esters with low catalyst loading as illustrated for the examples in FIG. 1. The fact that phosphine-containing species can catalyze borylation is important because numerous phosphines are commercially available. Consequently, the selectivities can be altered as a function of the phosphine that is added.

Another virtue of the present invention is that a broad range of heteroatoms and functional groups are inert under borylation conditions as shown in Scheme 5.

Scheme 5

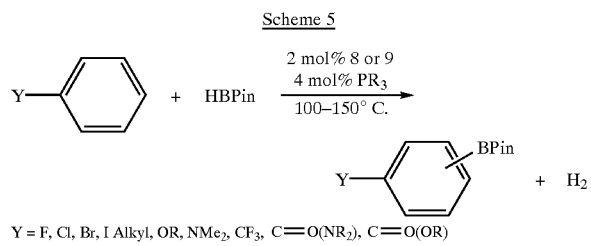

Y = F, Cl, Br, I Alkyl, OR, NMe₂, CF₃, C═O(NR₂), C═O(OR)

Given that Grignard reagents react with several of these groups and Pd catalyzes the formation of ArBPin from ArBr and HBPin, the functional group tolerance for the Ir-catalyzed chemistry is remarkable. Under appropriate conditions, even iodobenzene can be borylated without iodide reduction. In this instance, no conversion was observed when using precatalyst 8, whereas precatalyst 9 gives the borylated products in 95% yield as shown in Scheme 6.

Scheme 6

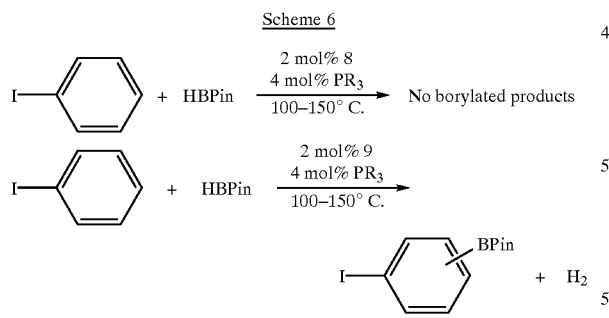

Therefore, the present substrate compatibility, which is already remarkably broad, is expected to expand with further improvements to the present invention.

For monosubstituted arenes, mixtures of meta and para borylated products are obtained. In contrast to the known Rh complexes that catalyze aromatic borylation, the meta:para ratio deviates significantly from 2:1. For most substrates, this ratio exceeds 3:1 and data for anisole are shown in Table 1.

TABLE 1

Isomer distributions for catalytic borylations of anisole

| Entry | Catalyst | Temp (° C.) | Time (h) | o:m:p |
|---|---|---|---|---|
| 1 | 2 mol % 8/2 PMe₃ | 150 | 29 | 9:74:17 |
| 2 | 2 mol % 9/2 PMe₃ | 150 | 41 | 8:75:17 |
| 3 | 2 mol % 8/dppe | 150 | 22 | 3:76:21 |
| 4 | 2 mol % 9/dppe | 150 | 51 | 3:78:20 |
| 5 | 2 mol % 8/dppe | 100 | 22 | 2:80:18 |
| 6 | 2 mol % 3/dppe | 100 | 18 | 2:80:18 |
| 7 | 2 mol % 9 | 150 | 3 | 12:53:36[a] |
| 8 | 2 mol % 8/PMe₃ | 150 | 29 | 2:57:40 |
| 9 | 2 mol % 9/PMe₃ | 150 | 40 | 3:67:30 |

[a]Low conversion.
o is ortho, m is meta, and p is para.
Dppe is 1,2-bis(diphenylphosphino)ethane It is noteworthy that the para isomer is more favored for entries 7 and 8, where the meta:para ratio is significantly less than 2:1. These data show that while there is a steric bias against ortho borylation, the meta:para ratio is sensitive to the type and amount of phosphine ligands that are added. For dppe, the activity at 100° C. is relatively high, and the reaction is complete in less time than at 150° C.

With the exception of F, and amide functional groups in some Rh catalyzed reactions, borylation at positions that are ortho to functional groups are avoided. Thus, 1,3-substituted aromatics can be selectively borylated at the 5' position. This is the hardest position to selectively activate by traditional aromatic substitution chemistry and for electron rich arenes, there are no general methods for preparing derivatives from the 1,3-substituted arenes.

Furthermore, multiple borylation of 1,3-substituted arenes does not occur to a significant extent, which means that equimolar quantities of borane and arene give aromatic boronic esters in high yield in the absence of solvent. Substrates that have been successfully converted to boronate esters under these conditions are shown in scheme 7.

Scheme 7

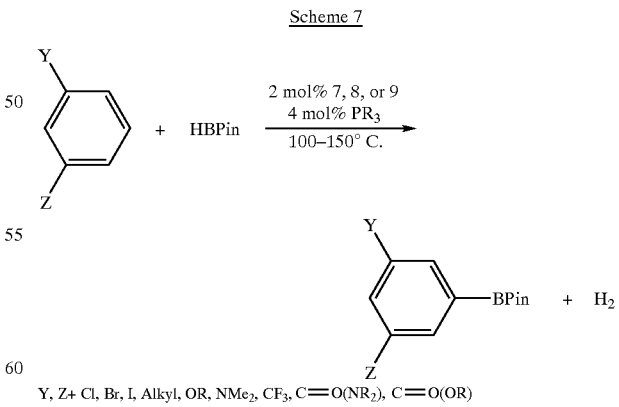

Y, Z+ Cl, Br, I, Alkyl, OR, NMe₂, CF₃, C═O(NR₂), C═O(OR)

For fluorinated benzenes, the borylation at ortho positions occurs readily. Hence, C₆HF₅ and 1,3,5-trifluorobenzene give mono and triborylated products, respectively, as shown in Scheme 8.

Scheme 8

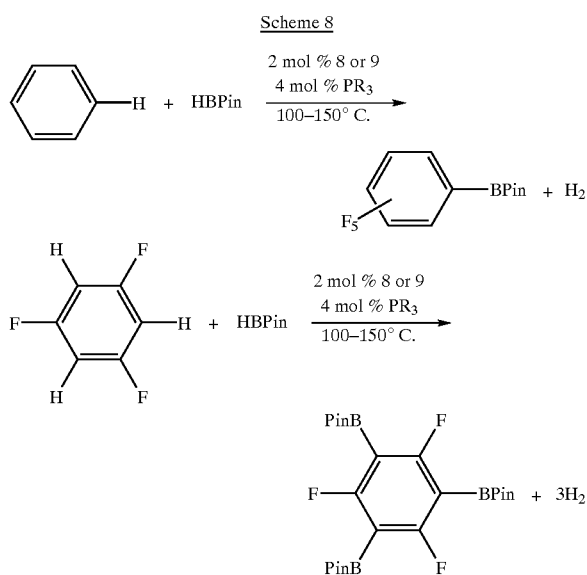

It is noteworthy that present Rh catalysts are not compatible with halide functionalities and substantial quantities of dehalogenated and diborylated products are observed. We extended the chemistry to five-membered rings and heterocycles as shown by the borylation of a protected pyrrole and 2,6-lutidine in Scheme 9.

Scheme 9

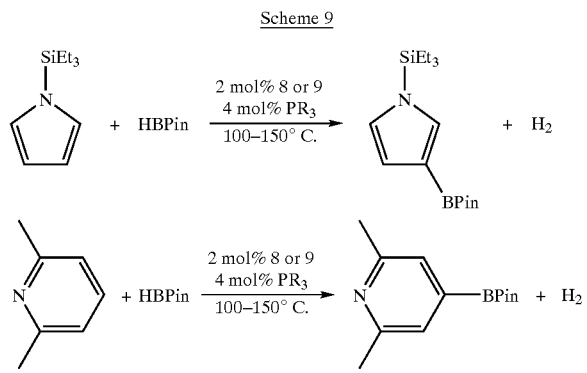

The borylation of aromatic and heteroaromatic compounds and the catalysts suitable for the borylation are disclosed in the commonly owned U.S. Application, which was filed Jul. 13, 2002, and which claims priority to U.S. Provisional 60/305,107 filed Jul. 13, 2001.

In the second step of the process of the present invention, the borylated intermediate is reacted with a halogenated aryl or organic, triflate, or nonaflate compound in the presence of a metal catalyst which cross-couples the C at the C—B bond and the C at the C-halogen bond to produce the substituted aromatic, heteroaromatic, biaryl, or biheteroaryl compound. In a preferred embodiment, the metal comprising the metal catalyst is palladium. Examples of Pd catalysts which are suitable for the cross-coupling include, but are not limited to, $Pd(PPh3)_4/P(^tBu)_3$, $PdCl_2(dppf)$ $Pd(OAc)_2/PCy_3$ wherein P is phosphorus and Ph is phenyl, dba is dibenzylideneacetone, $^tBu$ is tert-butyl, and dppf is diphenylphosphinoferrocene.

The process for making organic substituted aromatic and heteroaromatic compounds, including biaryls and biheteroaryls, avoids many of the limitations of the prior art because (1) the borylation reactions can be carried out in neat substrates, thereby avoiding ethereal solvents, (2) since the C—H bonds are selectively activated, halogenation of arenes and conversions to Grignard or organolithium reagents are eliminated, (3) the only byproducts of the borylation reaction are hydrogen, which is easily removed, and the catalyst, which is present in low concentrations, can be recovered, (4) the process of the present invention tolerates a broad range of functional groups, (6) active catalysts are generated from common precursors and selectivities can be altered by adding commercially available ligands such as alkyl phosphines, (7) particular substitution patterns which are notoriously difficult to achieve using prior art aromatic substitution chemistry can be obtained in one step starting from inexpensive starting materials, and (8) Ir metal is relatively inert, Ir complexes generally have low toxicity, and Ir metal recovered from the reactions can be recovered from the reaction waste and recycled. Furthermore, the process can be used to make chiral organic substituted aromatic compounds.

The following examples are intended to promote a further understanding of the present invention.

EXAMPLE 1

The process of the present invention was inspired by Bergman's (Science 223: 902–908 (1984)) and Jones and Feher's (Acc. Chem. Res. 22: 91–100 (1989)) fundamental studies of hydrocarbon (R—H, R=alkyl or aryl) activation by $Cp^*(Me_3)M^I$ intermediates (M=Ir, Rh; $Cp^*$ $\eta^5$-$C_5Me_5$), which produce $Cp^*(PMe_3)M^{III}(H)(R)$ where M—H and M—R bonds result from R—H scission.

While investigating stoichiometric B—C bond formation in reactions between $Cp^*(PMe_3)Ir(H)(Ph)$ and pinacolborane (HBPin), we found that substantial quantities of arylboron products were produced from catalytic solvent activation. The major metal-containing product in this reaction, $Cp^*(PMe_3)Ir(H)(BPin)(2)$, was a precatalyst for benzene borylation with an effective turnover number (TON) corresponding to the formation of three molecules of PhBPin per molecule of 2 (Iverson and Smith, III, J. Am. Chem. Soc. 121: 7696–7697 (1999)). Subsequently, Hartwig and co-workers reported alkane and arene borylations utilizing much more active Rh precatalysts, such as $Cp^*Rh(\eta^4$-$C_6Me_6)$ (7)(Chen et al., Science 287: 1995–1997 (2000)).

A comparison of precatalysts 2 and 7 in borylations of various substituted arenes revealed that the Ir system was more selective towards arene C—H activation (Cho et al., J. Am. Chem. Soc. 122: 12868–12869 (2000)). Given the importance of selectivity in chemical synthesis, these findings spurred a detailed investigation of the original Ir system. Those results are described herein.

Compound 2 is stable in benzene solutions after prolonged thermolysis, which eliminates several mechanistic possibilities, including $PMe_3$ dissociation to generate $Cp^*Ir(H)(BPin)$, an analog of proposed intermediates in the Rh system. However, added $PMe_3$ strongly inhibits catalysis where HBPin is present. This indicated that small quantities of phosphine-$Ir^V$ species could be active. Since $Cp^*IrH_{4-x}(BPin)_x$ species (x=1, 2) form in the thermolysis of $CP^*IrH_4$ and HBPin (Kawamura and Hartwig, J. Am. Chem. Soc. 123: 8422–8423 (2001)), anisole borylations with identical loadings of $CP^*IrH_4$ and 2 were compared. From this experiment, $Cp^*IrH_{4-x}(BPin)_x$ intermediates can be eliminated because they are not kinetically competent for catalysis and the borylation regioselectivities for $Cp^*IrH_4$ and 2 differ substantially. At 150° C., the following isomer ratios were obtained for anisole borylation with 20 mol % precatalyst loadings: Cp*IrH$_4$, o:m:p=3:49:48; 2 o:m:p= 2:79:19.

Exclusion of a simple phosphine dissociative pathway narrows the plausible catalysts to two choices: (i) Ir phosphine species arising from Cp* loss or (ii) species where both Cp* and PMe$_3$ have been lost. The latter possibility was intriguing in light of Marder's synthesis of (η$^6$-arene)Ir (BCat)$_3$ complexes (Cat=ortho-catecholate) from (Ind)Ir (COD) (3, Ind η$^5$-C$_9$H$_7$, COD=1,5-cyclooctadiene) and HBCat in arene solvents (10). Using an analogous route, we prepared (η$^6$-mesitylene)Ir(BPin)$_3$ (9 in which B(OR)$_2$ is BPin) in 19% yield from (Ind)Ir(COD) (8) and HBPin (Compound 9 has been prepared as an analytically pure white solid. Relevant spectroscopic data included $^1$H NMR (C$_6$D$_6$) δ1.33 (s,36 H, BO$_2$C$_6$H$_{12}$), 2.23 (s, 9H, C$_6$H$_3$ (CH$_3$)$_3$), 5.62 (s, 3H, C$_6$H$_3$(CH$_3$)$_3$). $^{11}$B NMR (C$_6$D$_6$) δ 32.5. $^{13}$C NMR (C$_6$D$_6$) δ 19.68, 25.73, 80.95, 96,97, 118.05). Compound 9 reacted with benzene at 150° C. to produce Ir metal and three equivalents of C$_6$H$_5$BPin, but did not catalyze C$_6$H$_5$BPin formation from benzene and HBPin. Thus, it appears that phosphines or related donor ligands are required for catalysis.

Utilizing the lability of the mesitylene ligand in 9, Ir phosphine species were generated in situ from 9 and appropriate phosphines and subsequently screened for activity. Borylation using 2 mol % 9 and 4 mol % PMe$_3$ was viable (Table 1, entry 1), and both catalytic activity and TONs for benzene borylation increased dramatically relative to precatalyst 2. Borylation rates were appreciable when P:Ir<3:1, but decreased dramatically when P:Ir ratio equals or exceeds 3:1.

TABLE 1[a]

| Ent. | Sub. | Arene:HBPin | Prod. | Cat. | Ligand | Temp (° C.) | Time (h) | Yield (%) |
|---|---|---|---|---|---|---|---|---|
| 1 | C$_6$H$_6$ | 16:1 | PhBPin | (MeSH) Ir (BPin)$_3$ (9) | PMe$_3$ | 150 | 15 | 98[b] |
| 2 | C$_6$H$_6$ | 16:1 | PhBPin | (Ind)Ir(COD) (8) | PMe$_3$ | 150 | 18 | 88[b] |
| 3 | C$_6$H$_6$ | 16:1 | PhBPin | 8 | dppe | 150 | 2 | 95[b] |
| 4 | C$_6$H$_6$ | 16:1 | PhBPin | 8 | dmpe | 150 | 2 | 84 |
| 5 | C$_6$H$_6$ | 16:1 | PhBPin | 0.02 mol % 8 | dmpe | 150 | 61 | 90[b] |
| 6 | C$_6$H$_6$ | 16:1 | PhBPin | (IrCl(COD))$_2$ | dmpe | 150 | 8 | 74[b] |
| 7 | 1,3,5-trifluorobenzene | 4:1 | 2,4,6-trifluorophenyl-BPin | 8 | dmpe | 150 | 1 | 63 |
| 8 | 1,3,5-trifluorobenzene | 1:5 | 1,3,5-trifluoro-2,4,6-tris(BPin)benzene | 8 | dmpe | 150 | 62 | 76 |
| 9 | 1,4-difluorobenzene | 4:1 | 2,5-difluorophenyl-BPin | 8 | dppe | 100 | 3 | 81 |
| 10 | 1,4-dichlorobenzene | 1:1.5 | 2,5-dichlorophenyl-BPin | 8 | dppe | 100 | 14 | 89 |
| 11 | 1,3-dibromobenzene | 1:1.5 | 3,5-dibromophenyl-BPin | 8 | dppe | 100 | 17 | 92 |

TABLE 1a-continued

| Ent. | Sub. | Arene:HBPin | Prod. | Cat. | Ligand | Temp (° C.) | Time (h) | Yield (%) |
|---|---|---|---|---|---|---|---|---|
| 12c | 2,6-dichloropyridine | 1:2 | 4-BPin-2,6-dichloropyridine | 8 | dppe | 100 | 4 | 69 |
| 13 | iodobenzene | 10:1 | — | 8 | dppe | 100 | 60 | — |
| 14 | iodobenzene | 10:1 | PinB-C6H4-I (m:p = 79:21) | 9 | dppe | 100 | 57 | 77 |
| 15c | methyl 3-chlorobenzoate | 1:2 | BPin-substituted methyl 3-chlorobenzoate | 8 | dppe | 100 | 25 | 95 |
| 16 | 1,2-dimethoxybenzene | 1:3 | 4-BPin-1,2-dimethoxybenzene | 8 | dmpe | 150 | 95 | 82 | aReactions run in neat arene, Ir = 2 mol %, P: Ir = 2:1, and yields are reported for isolated materials unless otherwise noted. (COD = 1,5,-cyclooctadiene, dmpe = $Me_2PCH_2CH_2PMe_2$, dppe = $Ph_2PCH_2CH_2PPh_2$).
bGC yield base on HBPin.
cReactions run in cyclohexane.

The low isolated yields of 9 hampered screening efforts and precluded practical applications despite the dramatic improvement in catalytic activity. Hence, we sought alternative means for generating active catalysts. Since NMR spectra indicated quantitative generation of 9 from 8, in situ generation of active catalysts by phosphine addition to 8 was examined. Compound 8 was synthesized in 86% yield from indenyl lithium and $(IrCl(COD))_2$ (Merola and Kacmarcik, Organometallics 8: 778–784 (1989)). This approach was successful and results for benzene borylations are shown in Table 1 (entries 2–5). Chelating phosphines substantially increased activity and TONs as highlighted for 1,2-bis(dimethylphosphino)ethane (dmpe) where the effective TON of 4500 (entry 5) represented an improvement of more than 1000-fold over precatalyst 2. In addition, active catalysts were generated from commercially available sources such as $(IrCl(COD))_2$ (entry 6).

If the primary active species generated by $PMe_3$ addition to 8 and 9 are identical to those generated from 2, borylations of substituted benzenes should exhibit similar regio- and chemoselectivities. Anisole is a useful substrate for probing regioselectivity and the meta:para ratios determined from borylations by active species generated by $PMe_3$ addition to 8 and 9 are similar to those for 2 (For catalysts generated from 4 mol % $PMe_3$ and 2 mol % 8 or 9, the following isomer ratios were obtained for anisole borylation at 150° C.: 8, o:m:p=9:74:17; 9, o:m:p=8:75:17. For 8 and 9, ortho borylation increases slightly, which could signify a minor pathway that is not accessible from 2).

To assess chemoselectivities, the ratios of arene to benzylic activation in M-xylene were examined. The selectivities of catalysts generated from 8 (13:1) and 9 (12:1) were diminished relative to the selectivity of precatalyst 2 (35:1). Nevertheless, the Ir catalysts were more selective for arene activation than the Rh catalyst, 7, where the selectivity was 7:1 (Cho et al., J. Am. Chem. Soc. 122: 12868–12869 (2000)); a Rh catalyst that is highly selective for benzylic borylation has been recently reported (Shimada et al., Angew. Chem., Int. Ed. 40: 2168–2171 (2001)), and the addition of one equivalent of the chelating phosphine, 1,2-bis(diphenylphosphino)ethane (dppe) per equivalent of 8 or 9 generated catalysts where the arene to benzylic selectivities exceeded 142:1.

Dramatic differences in chemoselectivities between Ir and Rh catalysts were found for halogenated substrates, where the Ir catalysts preferentially activated C—H bonds. A representative procedure for borylation is given for entry 10 of Table 1. Briefly, in a glove box under $N_2$, compound 8 (57 mg, 0.14 mmol) and dppe (54 mg, 0.14 mmol) were dissolved in HBPin (1.30 g. 10.2 mmol). The solution was transferred to a thick-walled air-free flask containing 1,3-dichlorobenzene (1.00 g, 6.80 mmol). The clear yellow solution was heated at 100° C. under $N_2$ and monitored by GC-FID. After 14 hours, the reaction mixture was pumped down to obtain a brown oil, which was vacuum distilled at 93–94° C. (0.03 mmHg). The resulting oil was then dissolved in $Et_2O$ (10 mL) and washed with water (5×100 mL).

After drying over MgSO$_4$, ether was removed under high-vacuum to give 1.65 g (89% yield) of colorless 1,3,5-C$_6$H$_3$Cl$_2$BPin (mp 36–38° C.: $^1$H NMR (500 MHz. CDCl$_3$) δ 1.32 (s, 12H), 7.41 (t, J=2.0 Hz, 1H), 7.63 (d, J=2.0 Hz, 2H). $^{13}$C NMR (125 MHz, CDCl$_3$) δ 24.82, 84.49, 131.1, 133.7, 134.7. $^{11}$B NMR (CDCl$_3$) δ 30). Good yields of mono- or tri-borylated products of 1,3,5-trifluorobenzene were obtained by adjusting the arene:HBPin ratio (Table 1, entries 7 and 8). In contrast, previous attempts to effect multiple borylations of 1,3,5-trifluorobenzene using the Rh catalyst 7 led to increased defluorination (Cho et al., J. Am. Chem. Soc. 122: 12868–12869 (2000)). Borylations of aromatics with heavier halogen substituents provided an even starker contrast between Ir and Rh catalysts. For example, Ir catalyzed borylations of 1,3-dichlorobenzene and 1,3-dibromobenzene generate meta functionalized products in high yields (entries 10 and 11), while dehalogenation is the dominant pathway in Rh catalyzed reactions. Dechlorination was observed during attempted silylations of 1,3-dichlorobenzene using closely related Rh catalysts (Ezbiansky et al., Organometallics 17: 1455–1457 (1998). The finding that aromatic C-halogen bonds survived in the Ir catalyzed reactions contrasted the Pd-catalyzed reactions of boranes and aryl bromides where the C—Br bonds were converted to C—B or C—H bonds (Murata, et al., J. Org. Chem. 65: 164–168 (2000)). Entry 12 illustrates an extension of meta selective borylation to a halogenated heterocycle.

Since aryl iodides have the weakest carbon-hydrogen bonds, they are most susceptible towards reductive cleavage by transition metals. Hence, it is not surprising that the Ir catalysts generated from 8 were ineffective in aromatic borylation of iodobenzene (Table I, entry 13). However, iodobenzene and HBPin reacted smoothly to yield a mixture of C$_6$H$_4$I(BPin) isomers when active catalysts were generated from the Ir$^{III}$ source, 9, and dppe (entry 14). Thus, Ir catalysts are compatible with the entire range of aryl halides. Furthermore, functional group tolerance that was previously found in Rh catalyzed borylations extends to Ir catalyzed reactions (viz., ester compatibility in entry 15) and Ir selectively borylates symmetrical 1,2-substituted arenes at the 4-position (entry 16).

Figure 3A:
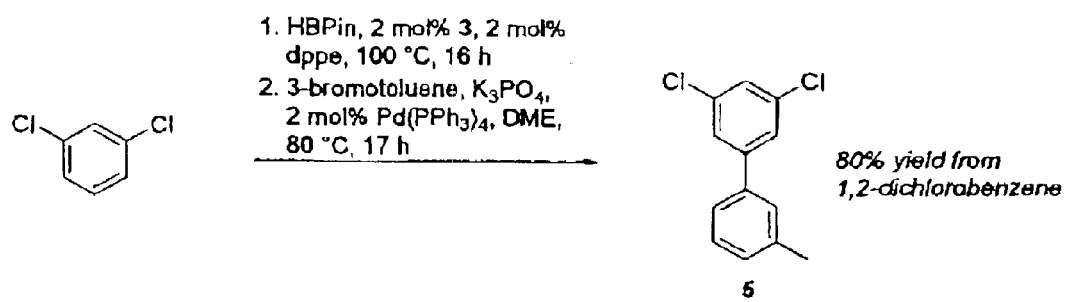
FIG. 3A shows an example of the one vessel C—H activation/cross coupling reactions as applied to biaryl synthesis.
Figure 3B:
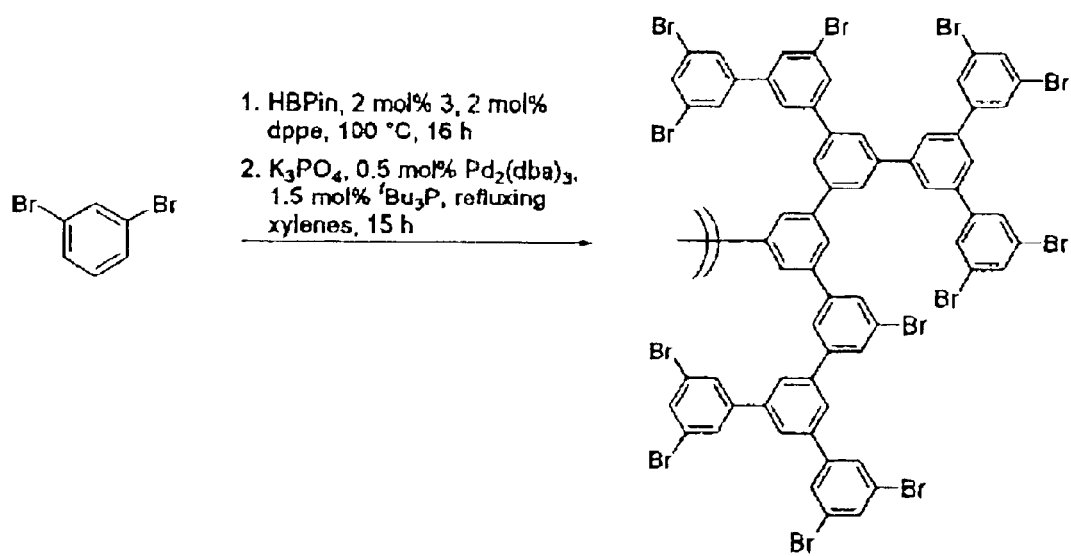
FIG. 3B shows an example of the one vessel C—H activation/cross coupling reactions as applied to polyphenylene synthesis.

The remarkable selectivity of Ir borylation catalysts for aromatic C—H bonds suggested that Ir byproducts might not interfere in subsequent reactions of the arylboron products. Thus, we envisaged one-vessel elaborations of arene C—H bonds where catalytic borylations are followed by other metal-catalyzed events in a catalytic cascade. For a Zr/Pd catalyzed route to substituted biphenyls and terphenyls (See Frid et al., J. Am. Chem. Soc. 121: 9469–9470 (1999)). To assess this possibility, the union of catalytic borylations and Miyaura-Suzuki cross-couplings for one-vessel biaryl synthesis from C—H and C—X precursors was attempted. As shown in FIG. 3A, the biaryl product can be prepared in good yield from the in situ Pd-catalyzed cross-coupling of 3-bromotoluene with 1,3,5-C$_6$H$_3$Cl2(BPin), generated by Ir-catalyzed borylation of 1,3-dichlorobenzene with HBPin. An interesting extension of Ir/Pd tandem catalysis highlighting Ir compatibility with halogenated aromatics is shown in FIG. 3B. The specific target was a hyperbranched polyphenylene that Kim and Webster prepared via Pd catalyzed coupling of the bromo/boronic acid monomer, 1,3,5-C$_6$H$_3$Br$_2$(B(OH)$_2$) (Kim and Webster, Macromolec. 25: 5561–5572 (1992)). Using Ir/Pd tandem catalysis, material with nearly identical NMR ($^{13}$C, $^1$H) and GPC data was obtained from HBPin and 1,3-dibromobenzene in a one-vessel reaction. For the material in FIG. 3B, M$_ω$=6374 and M$_n$=3460 as compared to the previously reported values of M$_ω$=5750 and M$_n$=3820 (Kim and Webster, Macromolec. 25: 5561–5572 (1992)).

From a mechanistic standpoint, catalytic cycles involving oxidative addition/reductive elimination from Ir$^{I/III}$ and/or Ir$^{III/V}$ intermediates are consistent with the results herein. Within this context, we considered Ir$^I$ and Ir$^{III}$ boryl intermediates to be the most likely C—H activating species in the Ir$^{I/III}$ and Ir$^{III/V}$ cycles, respectively. Hence, the Ir$^I$ and Ir$^{III}$ boryl complexes, Ir(BPin)(PMe$_3$)$_4$ and fac-Ir(BPin)$_3$(PMe$_3$)$_3$, were prepared in order to evaluate their stoichiometric reactions with arenes.

Compounds Ir(BPin)(PMe$_3$)$_4$ and fac-Ir(BPin)$_3$(PMe$_3$)$_3$ have been fully characterized as shown by the following spectroscopic data: Ir(BPin)(PMe$_3$)$_4$, $^1$H NMR (C$_6$D$_6$, 25° C.) δ 1.24 (s, 12H, BO$_2$C$_6$H$_{12}$), 1.58 (b, 36H, PCCH$_3$)$_3$). $^{11}$B NMR (C$_6$D$_6$) δ 38. $^{31}$P {$^1$H} NMR (C$_6$D$_6$) δ -57.5; fac-Ir(BPin)$_3$(PMe$_3$)$_3$, $^1$H NMR (C$_6$D$_6$) δ 1.34 (S, 36H, BO$_2$C$_6$H$_{12}$), 1.52 (m, 27H, P(CH$_3$)$_3$). $^{11}$B NMR (C$_6$D$_6$) δ 36.0. $^{31}$P{$^1$H} NMR (C$_6$D$_6$) δ -64. In reactions with arenes, compounds Ir(BPin)(PMe$_3$)$_4$ and fac-Ir(BPin)$_3$(PMe$_3$)$_3$ both reacted cleanly with benzene to produce PhBPin and the corresponding hydride complexes shown below, which was consistent with the idea that Ir$^I$ or Ir$^{III}$ species can effect arene borylation; however, the arene products from stoichiometric reactions of Ir(BPin)(PMe$_3$)$_4$ and fac-Ir(BPin)$_3$(PMe$_3$)$_3$ with iodobenzene differed substantially.

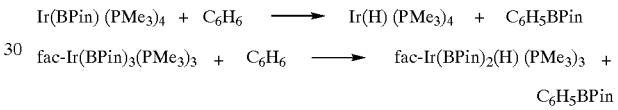

Specifically, compound Ir(BPin)(PMe$_3$)$_4$ reacted rapidly with iodobenzene at room temperature, but isomers of C$_6$H$_4$I(BPin) were not detected, even after prolonged thermolysis. Conversely, thermolysis of fac-Ir(BPin)$_3$(PMe$_3$)$_3$ in iodobenzene produced m- and p-C$_6$H$_4$I(BPin) in 54% yield, based on fac-Ir(BPin)$_3$(PMe$_3$)$_3$, in addition to a 45% yield of PhBPin.

Since conversion rates in catalytic reactions plummet when P:Ir ratios equal or exceed 3:1, the observation that Ir(BPin)(PMe$_3$)$_4$ and fac-Ir(BPin)$_3$(PMe$_3$)$_3$ were not kinetically competent for catalysis was expected. However, this does not exclude the possibility that identical intermediates are generated in the stoichiometric and catalytic reactions. Instead, generation of appropriate intermediates under catalytic conditions could simply be more efficient. Nevertheless, the stoichiometric transformations lend credence to either Ir$^I$ or Ir$^{III}$ species mediating C—H activations under catalytic conditions. The reactions of Ir(BPin)(PMe$_3$)$_4$ and fac-Ir(BPin)$_3$(PMe$_3$)$_3$ with iodobenzene have greater mechanistic implications. For example, the absence of C$_6$H$_4$I(BPin) products in thermolysis of Ir(BPin)(PMe$_3$)$_4$ mirrored the failed attempt to borylate iodobenzene using the Ir$^I$ precatalyst 8 (entry 13). The reactivity of fac-Ir(BPin)$_3$(PMe$_3$)$_3$ suggests that an Ir$^{III}$ intermediate may activate C—H bonds in the presence of C—I bonds, but the chemistry of Ir(BPin)(PMe$_3$)$_4$ is more important because it essentially excludes the participation of Ir$^I$ species in the successful borylation of iodobenzene using the Ir$^{III}$ precatalyst 9 (entry 14).

Figure 4:
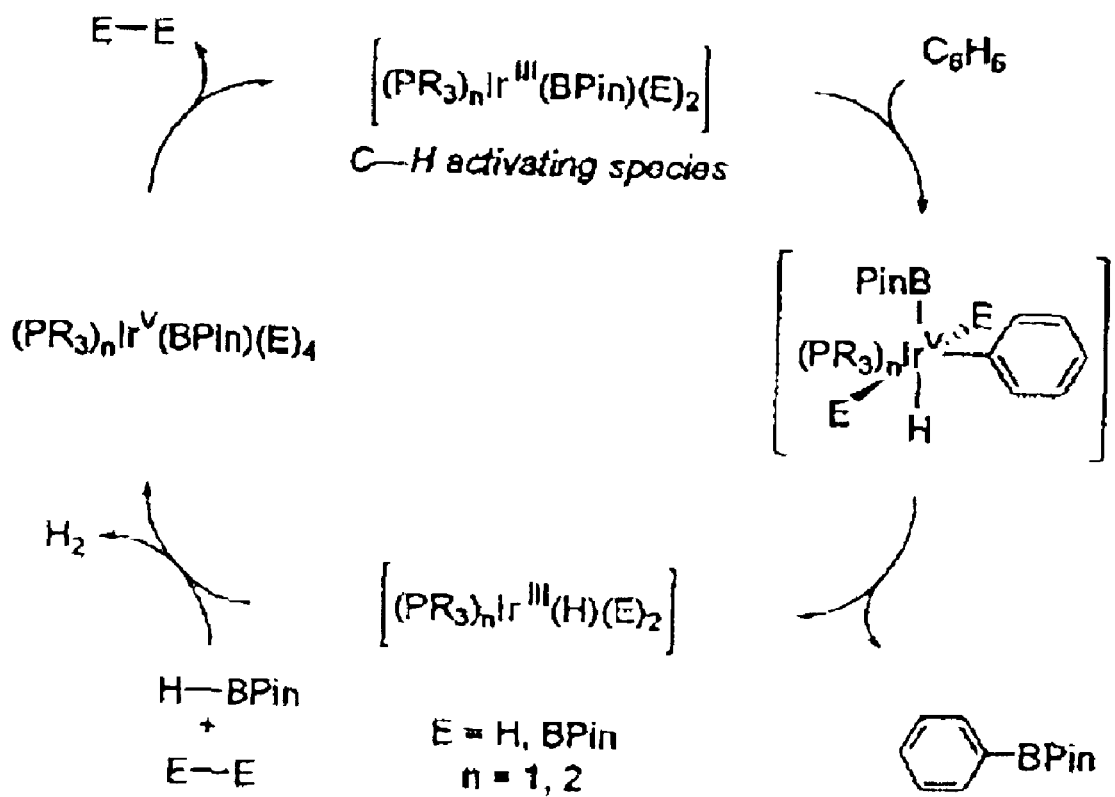
FIG. 4 shows a mechanism for aromatic borylations catalyzed by Ir boryl complexes.

Although catalytic processes involving Ir$^I$ intermediates have not been categorically excluded, we presently prefer the simplified mechanism involving Ir$^{III}$ and Ir$^V$ intermediates in FIG. 4 for the following reasons: (i) the correlations between stoichiometric and catalytic borylations of iodobenzene by $Ir^I$ and $Ir^{III}$ argue against an $Ir^{I/III}$ mechanism, (ii) the catalytic inhibition when P:Ir ratios equal or exceed 3:1 and the slow borylation rates for the 18-electron $Ir^{III}$ complex fac-Ir(BPin)$_3$(PMe$_3$)$_3$ are consistent with the generation of a reactive 16-electron bisphosphine $Ir^{III}$ intermediate from an 18-electron bisphosphine $Ir^V$ resting state, (iii) since chelating phosphines generally inhibit phosphine dissociative pathways, the catalytic activity with chelating phosphines supports the viability of bisphosphine intermediates, and (iv) the 18-electron bisphosphine compound, Ir(PMe$_3$)$_2$H$_5$, is an effective precatalyst for borylation. A more definitive characterization of the catalytic manifold is underway.

In summary, an investigation of the original Ir catalytic system, whose promising selectivities could not be practically implemented due to extremely low effective TONs, has produced a family of efficient borylation catalysts with remarkable regio- and chemoselectivities. In addition to providing a direct route to aryl and heteroaryl boron compounds from boranes and arenes, the viability of a tandem catalytic cascade where the first step is an Ir catalyzed aromatic borylation has been demonstrated. We are optimistic that extensions of these findings will have significant synthetic applications.

EXAMPLE 2

This example shows a two-step, one-vessel process for synthesis of the biaryl 3,5-bis(trifluoromethyl)biphenyl from 1,3-bis(trifluoromethyl)benzene, a borane (HBPin), and iodobenzene. An arylboronate ester was produced using an Ir catalyst and the arylboronate was subsequently coupled to the iodobenzene using a palladium catalyst.

In a glove box, HBPin (448 mg, 3.50 mmol) was added to a mixture of 1,3-bis(trifluoromethyl)benzene (500 mg, 1.34 mmol), (COD) Ir(Indenyl) (19.5 mg, 0.047 mmol), and dppe (18.6 mg, 0.047 mmol) in a small air-free flask equipped with a stir bar. The flask was then sealed and heated at 100° C. for 16 hours.

Afterwards, the reaction solution was allowed to cool to room temperature and Pd$_2$(dba)$_3$ (42.8 mg, 0.047 mmol), P(tBu)$_3$ (28.3 mg 0.140 mmol), iodobenzene (476 mg, 2.24 mmol), K$_2$PO$_4$ (744 mg, 3.50 mmol), and DME (10 mL) were added. The mixture was stirred at 80° C. for 3 hours. The 3,5-bis(trifluoromethyl)biphenyl was obtained (68.2% yield) as a colorless oil. The identity of the 3,5-bis (trifluoromethyl)biphenyl was confirmed by comparison to the GC retention time and $^1$H NMR data to an authentic sample prepared from 3,5-bis(trifluoromethyl)phenyl pinacolborane and iodobenzene. $^1$H NMR (CDCl$_3$, 300 MHz) δ 8.00 (s, 2H), 7.93 (s, 1H), 7.85–7.58 (m, 2H), 7.53–7.42 (m, 3H).

EXAMPLE 3

This example shows a closed system for a two-step, one-vessel process for synthesis of a biphenyl from benzene, a borane (HBPin), and a halogenated phenyl (PhI). An arylboronate ester was produced using an Ir catalyst and the arylboronate was subsequently coupled to the halogenated phenyl using a palladium catalyst.

In a glove box, benzene (437 mg, 5.60 mmol), Ir(COD) (Indenyl) (3.0 mg, 0.0070 mmol), dppe (2.8 mg, 0.0070 mmol), dodecane (internal standard, 11.5 mg, 0.0675 mmol), and HBPin (45 mg, 0.352 mmol) were added to a J. Young tube equipped with a stir bar. The tube was then sealed, removed from the box, and heated at 100° C. for 18 hours. A GC trace of the reaction mixture revealed PhBPin in 85.7% yield.

Next, the reaction solution was allowed to cool to room temperature and Pd(PPh$_3$)$_4$ (8.1 mg, 0.007 mmol), K$_3$PO$_4$ (112 mg, 0.528 mmol), PhI (72.7 mg, 0.356 mmol) and DME (2 mL) were added. Three freeze-pump-thaw cycles were performed to remove residual oxygen and the reaction mixture was heated at 80° C. for two days. GC analysis showed 81.8% GC-yield of the biphenyl, 79.7% GC-conversion of the iodobenzene, and 79.1% conversion of the PhBPin.

EXAMPLE 4

This example shows an open system for a two-step, one-vessel process for synthesis of a biphenyl from benzene, a borane (HBPin), and a halogenated phenyl (PhI). An arylboronate ester was produced using an Ir catalyst and the arylboronate was subsequently coupled to the halogenated phenyl using a palladium catalyst.

In a glove box, benzene (1.0 mL, 11.2 mmol), Ir(COD) (Indenyl) (3.0 mg, 0.0070 mmol), dppe (2.8 mg, 0.0070 mmol), dodecane (internal standard, 12.0 mg, 0.07 mmol), and HBPin (45 mg, 0.352 mmol) were added to a Schlenk tube equipped with a stir bar. The tube was then sealed, removed from the box, and heated at 100° C. for 18 hours with constant stirring.

Next, the reaction solution was allowed to cool to room temperature and Pd(PPh$_3$)$_4$ (8.5 mg, 0.0074 mmol), K$_3$PO$_4$ (112 mg, 0.528 mmol), PhI (74.9 mg, 0.367 mmol) and DME (2 mL) were added. A GC trace of the reaction mixture revealed PhBPin in 78.9% yield. The reaction mixture was then degassed by purging with nitrogen and stirred at 90–95° C. for 16.5 hours. A GC analysis showed a 97.3% yield of the biphenyl, 84.1% GC-conversion of the iodobenzene, and 90.7% conversion of the PhBPin.

EXAMPLE 5

This example shows an open system for a two-step, one-vessel process for synthesis of a biaryl from 1,3-dichlorobenzene, a borane (HBPin), and a 3-bromotoluene.

In a glove box, 1,3-dichlorobenzene, Ir(COD)(Indenyl) (2 mol %), dppe (2 mol %), and HBPin were added to a Schlenk tube equipped with a stir bar. The tube was then sealed, removed from the box, and heated at 100° C. for 16 hours with constant stirring.

Next, the reaction solution was allowed to cool to room temperature and Pd(PPh$_3$)$_4$ (2 mol %), K$_3$PO$_4$), 3-bromotoluene and DME (2 mL) were added. The reaction mixture was incubated at 80° C. for 17 hours. A CG analysis following the reaction showed an 80% yield of the biaryl from the 1,3-dichlorobenzene.

EXAMPLE 6

This example shows an open system for a two-step, one-vessel process for synthesis of a hyperbranched polyphenylene from 1,3-dibromobenzene.

In a glove box, 1,3-dibromobenzene, Ir(COD)(Indenyl) (2 mol %), dppe (2 mol %), and HBPin were added to a Schlenk tube equipped with a stir bar. The tube was then sealed, removed from the box, and heated at 100° C. for 16 hours with constant stirring.

Next, the reaction solution was allowed to cool to room temperature and Pd$_2$(dba)$_3$ (0.5 mol %), K$_3$PO$_4$, 3-bromotoluene, and $^t$Bu$_3$P, were added. The reaction mixture was incubated for 15 hours with refluxing xylenes. The hyperbranched polyphenylene was similar to that obtained by the process of Kim and Webster (Macromolec. 25: 5561–5572 (1992).

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

We claim:

1. A process for producing a substitute aromatic compound in one vessel, which comprises:
    (a) reacting in a reaction mixture first aromatic organic compound selected from the group consisting of an aryl, a six membered heteroaromatic compound, and a five membered heteroaromatic compound with a borane selected from the group consisting of a borane with a B—H, B—B, and B—Si bond in the presence of a catalytically effective amount of an iridium or rhodium complex with three or more substituents, and an organic ligand selected from the group consisting of phosphorus, carbon, nitrogen, oxygen, and sulfur organic ligands to form an aromatic boron compound in the reaction mixture; and
    (b) reacting the aromatic boron compound in the reaction mixture with a second aromatic organic compound selected from the group consisting of halide, triflate, and nonaflate in the presence of a catalytically effective, amount of a metal catalyst and in the presence of the iridium or rhodium, in the reaction mixture from step (a), wherein an aromatic group of the second aromatic organic compound is coupled to an aromatic group of the first aromatic organic boron compound to produce the substituted aromatic compound.

2. The process of claim 1, wherein the three or more substituents excludes hydrogen.

3. The process of claim 1 wherein the iridium complex with the ligand is selected from the group consisting of $(Cp^*)Ir(H)_2(Me_3P)$, $(Cp^*)Ir(H)(BPin)(Me_3P)$, $(Cp^*)Ir(H)(C_6H_5)(Me_3P)$, $(Ind)Ir(COD)$, $(Ind)Ir(dppe)$, $(MesH)Ir(BPin)(B(OR)_2)_2$, $((R_1)_3P)_3Ir(B(OR_2)_2)_3$, $(R_1)_2P)_2Ir(BPin)_3$, $(((R_1)_2P)_3Ir((R_2O)_2B)_3)_2$, $((R_1)_3P)_4Ir(BPin)$, $((R_1)_3P)_2Ir(BPin)_3$, $(MesH)Ir(BPin)_3$, and $(IrCl(COD))_2$, $(PMe_3)_2IrH_5$, $((R_1)_3P)_2IrH_5$, and $((R)_3P)_2IrH_x(B(OR_2)_2)_{5-x}$ where x is 0–4, wherein $Cp^*$ is 1,2,3,4,5-methylcyclopentadienyl, BPin is pinacolborane, Me is methyl, H is hydrogen, P is phosphorus, Ind is indenyl, COD is 1,5-cyclooctadiene, MesH is mesitylene, and wherein R, $R_1$, and $R_2$ are hydrogen, linear or branched alkyl containing 1 to 8 carbons, aryl, or a carbon in a cyclic structure.

4. The process of claim 1 wherein the iridium complex is (Ind)Ir(COD) wherein Ind is indenyl and COD is 1,5-cyclooctadiene.

5. The process of claim 1 wherein the iridium complex with the ligand is $(MesH)Ir(BPin)_3$ wherein MesH is mesitylene and BPin is pinacolborane.

6. The process of claim 1 wherein the iridium complex is $(IrCl(COD))_2$ wherein COD is 1,5-cyclooctadiene.

7. The process of claim 1 wherein the rhodium complex with the ligand is selected from the group consisting of $(Cp^*)Rh(H)_2(Me_3P)$, $(Cp^*)Rh(H)(BPin)(Me_3P)$ $(Cp^*)Rh(H)(C_6H_5)(Me_3P)$, and $(Cp^*)Rh(hexamethylbenzene)$, wherein $Cp^*$ is 1,2,3,4,5-methylcyclopentadienyl, BPin is pinacolborane, Me is methyl, H is hydrogen, and P is phosphorus.

8. The process of claim 1 or 2 wherein the phosphorus organic ligand is selected from the group consisting of trimethyl phosphine ($PMe_3$), 1,2-bis(dimethylphosphino)ethane (dmpe), $Ph_3P$, $Cy_3P$, and 1,2-bis(diphenylphosphino)ethane (dppe).

9. The process of claim 1 wherein the borane is a borane ester.

10. The process of claim 1, wherein the borane is pinacolborane.

11. The process of claim 1 wherein the metal is palladium.

12. The process of claim 1 wherein the metal catalyst complex is selected from $Pd(PPh_3)_4$, $Pd_2(dba)_3/P(^tBu)_3$, $PdCl_2(dppf)$, and $Pd(OAc)_2/Cy_3P$ wherein P is phosphorus and Ph is phenyl, dba is dibenzylideneacetone, $^tBu$ is tert-butyl, dppf is diphenylphosphinoferrocene.

13. A process for producing an organic substituted aryl or heteroaryl compound, which comprises:
    (a) reacting in a reaction mixture in a reaction vessel a first aromatic organic compound selected from the group consisting of an aryl, a six membered heteroaromatic compound, and a five membered heteroaromatic compound with a borane selected from the group consisting of a borane with a B—H, B—B and B—Si bond in the presence of a catalytically effective amount of an iridium or rhodium complex with three or more substituents, and an organic ligand selected from the group consisting of phosphorus, carbon, nitrogen, oxygen, and sulfur organic ligands to form an aromatic boron compound in the reaction mixture; and
    (b) reacting the aromatic boron compound in the reaction mixture in the reaction vessel with a second aromatic organic compound selected from the group consisting of halide, triflate, and nonaflate in the presence of a catalytically effective amount of a metal catalyst and in the presence of the iridum or rhodium in the reaction mixture from step (a) wherein an aromatic group of the second aromatic organic compound is coupled to an aromatic group of the firs aromatic organic boron compound to produce the organic substituted aryl or heteroaryl compound.

14. The process of claim 13 wherein the three or more substituents excludes hydrogen.

15. The process of claim 13 wherein the iridium complex with the ligand is selected from the group consisting of $(Cp^*)Ir(H)_2(Me_3P)$, $(Cp^*)Ir(H)(BPin)(Me_3P)$, $(Cp^*)Ir(H)(C_6H_5)(Me_3P)$, $(Ind)Ir(COD)$, $(Ind)Ir(dppe)$, $(MesH)Ir(BPin)(B(OR)_2)$, $((R_1)_3P)_3Ir(B(OR_2)_2)_3$, $(R_1)_3P)_2Ir(BPin)_3$, $(((R_1)_3P)_3Ir((R_2O)_2B)_3)_2$, $((R_1)_3P)_4Ir(BPin)$, $((R_1)_2P)_3Ir(BPin)_3$, $(MesH)Ir(BPin)_3$, $(PMe_3)_2IrH_5$, $((R_1)_3P)_2IrH_5$, and $((R_1)_3P)_2IrH_x(B(OR_2)_2)_{5-x}$, where x is 0–4, $(IrCl(COD))_2$, wherein $Cp^*$ is 1,2,3,4,5-methylcyclopentadienyl, BPin is pinacolborane, Me is methyl, H is hydrogen, P is phosphorus, Ind is indenyl, COD is 1,5-cyclooctadiene, MesH is mesitylene, and wherein R, $R_1$, and $R_2$ are hydrogen, linear or branched alkyl containing 1 to 8 carbons, aryl, or a carbon in a cyclic structure.

16. The process of claim 13 wherein the iridium complex is (Ind)Ir(COD) wherein Ind is indenyl and COD is 1,5-cyclooctadiene.

17. The process of claim 13 wherein the iridium complex with the ligand is $(MesH)Ir(BPin)_3$ wherein MesH is mesitylene and BPin is pinacolborane.

18. The process of claim 13 wherein the iridium complex is $(IrCl(COD))_2$ wherein COD is 1,5-cyclooctadiene.

19. The process of claim 13 wherein the rhodium complex is selected from the group consisting of $(Cp^*)Rh(H)_2(Me_3P)$, $(Cp^*)Rh(H)(BPin)(Me_3P)$, $(Cp^*)Rh(H)(C_6H_5)(Me_3P)$, and $(Cp^*)Rh(hexamethylbezene)$, wherein $Cp^*$ is 1,2,3,4,5-methylcyclopentadienyl, BPin is pinacolborane, Me is methyl, H is hydrogen, and P is phosphorus.

20. The process of claim 13 wherein the phosphorus organic ligand is selected from the group consisting of trimethyl phosphine ($PMe_3$), 1,2-bis(dimethylphosphino)ethane (dmpe), $Ph_3P$, $Cy_3P$, and 1,2-bis(diphenylphosphino)ethane (dppe).

21. The process of claim 13 wherein the borane is a borane ester.

22. The process of claim 13 wherein the borane is pinacolborane.

23. The process of claim 13 wherein the metal is palladium.

24. The process of claim 13 wherein the metal catalyst complex is selected from $Pd(PPh_3)_4$, $Pd_2(dba)_3/P(^tBu)_3$, $PdCl_2(dppf)$, and $Pd(OAc)_2/PCy_3$ wherein P is phosphorus and Ph is phenyl, dba is dibenzylideneacetone, $^tBu$ is tert-butyl, dppf is diphenylphosphinoferrocene.

* * * * *

UNITED STATES PATENT AND TRADEMARK OFFICE
CERTIFICATE OF CORRECTION

PATENT NO. : 6,867,302 B2
DATED : March 15, 2005
INVENTOR(S) : Milton R. Smith, III and Robert E. Maleczka It is certified that error appears in the above-identified patent and that said Letters Patent is hereby corrected as shown below:

<u>Column 6,</u>
Line 38, "Scheme 8" should be -- Scheme 1 --.

<u>Column 13,</u>
Line 61, "Pd(PPh3)4/P(tBu)3" should be -- Pd(PPh3)4 Pd2(dba)3, P(tBu)3 --.

<u>Column 19,</u>
Line 56, "1,3,5-$C_6H_3C12$" should be -- 1,3,5-$C_6H_3Cl_2$ --

<u>Column 23,</u>
Line 11, "a substitute aromatic" should be -- a substituted aromatic --.
Line 13, "mixture first" should be -- mixture a first --.

<u>Column 24,</u>
Line 35, "the firs" should be -- the first --.

Signed and Sealed this

Thirty-first Day of May, 2005

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,867,302 B2 | Page 1 of 1 |
| APPLICATION NO. | : 10/194859 | |
| DATED | : March 15, 2005 | |
| INVENTOR(S) | : Milton R. Smith, III et al. | |

It is certified that error appears in the above-identified patent and that said Letters Patent is hereby corrected as shown below:

In the Specification

In column 1, lines 15-19, please delete:

"This invention was supported in part by National Institutes of Health, National Institute of General Medical Sciences Grant No. R01 GM63188-01 and in part by National Science Foundation Grant No. CHE-9817230. The U.S. government has certain rights in this invention."

and insert:

-- This invention was made with government support under GM063188 awarded by the National Institutes of Health, and under CHE9817230 awarded by the National Science Foundation. The government has certain rights in the invention. --

Signed and Sealed this
Fifteenth Day of July, 2014

Michelle K. Lee
*Deputy Director of the United States Patent and Trademark Office*